(12) United States Patent
McNamara et al.

(10) Patent No.: US 7,777,871 B2
(45) Date of Patent: Aug. 17, 2010

(54) APPARATUS FOR MEASURING PHYSICAL PROPERTIES OF GOLF BALLS AND CORES

(75) Inventors: Michael McNamara, Fairhaven, MA (US); William Gobush, North Dartmouth, MA (US); Laurent Bissonnette, Portsmouth, RI (US)

(73) Assignee: Acushnet Company, Fairhaven, MA (US)

( * ) Notice: Subject to any disclaimer, the term of this patent is extended or adjusted under 35 U.S.C. 154(b) by 340 days.

(21) Appl. No.: 12/111,246

(22) Filed: Apr. 29, 2008

(65) Prior Publication Data

US 2009/0268215 A1   Oct. 29, 2009

(51) Int. Cl.
*G01J 3/443* (2006.01)

(52) U.S. Cl. ...................................................... 356/72

(58) Field of Classification Search .................. None
See application file for complete search history.

(56) References Cited

U.S. PATENT DOCUMENTS

| | | | |
|---|---|---|---|
| 4,520,595 A | 6/1985 | Diener | |
| 5,703,687 A | 12/1997 | Kumagai et al. | |
| 5,708,532 A | 1/1998 | Wartman | |
| 6,640,002 B1 * | 10/2003 | Kawada | 382/141 |
| 6,755,085 B1 | 6/2004 | Kazanjian et al. | |
| 6,839,138 B2 | 1/2005 | Welchman et al. | |
| 2007/0067976 A1 * | 3/2007 | Dvoskin et al. | 29/407.01 |

* cited by examiner

*Primary Examiner*—Tu T Nguyen
(74) *Attorney, Agent, or Firm*—D. Michael Burns

(57) ABSTRACT

A method and apparatus for an automated testing system that tests for physical properties of golf balls or golf ball cores. The apparatus includes an on-load magazine wherein golf balls or cores are loaded for pick and place feeding to holding nests defined in a rotary indexing table. The nests are removable and/or of multiple size accommodations to accept balls and cores from 1.00 to 1.72 inches. The system includes a diameter measuring station, a compression measuring station, and a weight measuring station. Through the rotary indexing table, the golf ball or core may be selectively dialed to one or more of the stations for testing. A computer analyzes the properties of each ball or core tested and correlates the data so that each ball is subsequently either passed to an off-load magazine or rejected.

19 Claims, 6 Drawing Sheets

APPARATUS FOR MEASURING PHYSICAL PROPERTIES OF GOLF BALLS AND CORES

FIELD OF THE INVENTION

The present invention generally relates to an apparatus and method of automating the testing of golf balls and golf ball cores. More particularly, the present invention relates to an automated apparatus for testing the diameter, compression and weight of golf balls or golf ball cores.

BACKGROUND OF THE INVENTION

The manufacture of golf balls typically involves a series of sequential processes performed at different processing stations, typically spatially separated one from another. For example, golf balls typically have a core and a dimpled pattern for a cover.

Each process must be carefully monitored for quality assurance purposes. Inspections are typically performed for assuring a desired confidence level in production quality. Quality control criteria, may be in place as well. The manufacturer may further choose to manually inspect the entire lot being inspected if a given number of defective balls are found therein. Moreover, if a major defect is found, such as a significant variance in a physical property like weight or compression which could affect performance or durability, the manufacturer may choose to shut down the entire system.

There has been a continuing desire to achieve high production rates. Because automated apparatus typically may function faster than human operators, there has been an ongoing goal to reduce, if not eliminate, human intervention during the manufacturing process. Thus, performance or physical property testing is typically performed at a separate automated processing station functioning at optimal efficiency and speed so that the overall production rate is maintained at the desired high level. For instance, given the quality control standards necessary to meet production standards and the high production rates of golf ball manufacturing plants, actions to correct a malfunction in the automated processing equipment should be taken as soon as possible to reduce the number of defective golf balls produced. The sooner a defect is detected, the lower the likelihood of reaching the pre-determined number of defects initiating a need for further quality assurance corrective measures that need to be taken. Accordingly, there is a need for speedy and efficient testing of physical properties of golf balls and golf ball cores so that any manufacturing problem may be corrected almost immediately to reduce the further production of defective balls.

A variety of automated inspection systems and methods are known for use in quality control of automated processing stations. Inspection apparatuses currently known for inspecting spherical objects generally require rotation of the object and cannot account for the three-dimensional contoured surface. For example, U.S. Pat. No. 5,703,687 to Kumagai et al. shows an automated inspection system which requires the addition of golf ball rotating equipment to the usual automated conveying equipment used to convey golf balls from an automated processing apparatus.

The spherical shape of the golf ball makes automated inspection of the three-dimensional surface difficult to achieve by the two-dimensional analysis techniques of inspection systems used in other industries. The addition of contours, in the form of dimples, on an already spherical object further complicates automated inspection thereof. Standard machine vision inspection systems using a template based inspection technique desensitized to prevent false rejections of prints or contoured surfaces are also de-sensitized to small defects on the edge of the print and thus are not completely effective. Prior art inspection systems have not been successful at achieving the proper combination of machine vision components, lighting, optics, and image processing techniques necessary to successfully analyze the printed images on golf balls to provide an on-line inspection system.

Thus, the golf ball manufacturing industry has heretofore relied on manual inspection to determine the quality of the various processes performed in manufacturing a golf ball. However, because the high production rate typically encountered in the industry far exceeds the speed with which manual inspection can be performed, such manual inspection cannot be performed on every ball, thus impeding efficiency, and potentially resulting in a certain number of undetected defective balls. Moreover, manual inspection is not 100% effective, given the possibility of human error or oversight, and may cause the inspected ball to be marred by manual handling.

Thus, although automation of the golf ball manufacturing process has resulted in high production rates, such production rates are subject to the efficiency and speed with which quality inspection may be performed. If inspection is not performed routinely and quickly, a high number of defective products may be produced before appropriate measures are taken to correct the cause of the defect.

SUMMARY OF THE INVENTION

In accordance with the principles of the present invention, an automated testing system is provided for the testing of physical properties of golf balls and golf ball cores. The apparatus includes an on-load magazine wherein golf balls or cores are loaded for feeding to a rotary indexing table. By a pick and place mechanism, each ball is positioned into one of a plurality of holding nests that are defined in the rotary indexing table. The nests are removable and/or sized to accept balls and cores from 1.00 to 1.72 inches. A multitude of nest sizes may be present on the rotary indexing table at the same time and a nest may accommodate a multitude of ball sizes. The apparatus includes a diameter measuring station, a compression measuring station, and a weight measuring station. The rotary indexing table is capable of being dialed such that a ball or core may be selectively presented for testing to any or all of the measuring stations. A computer analyzes the properties of each ball or core tested and correlates the data so that each ball is subsequently either passed to an offload magazine or rejected.

The automated apparatus of the present invention comprises an optical imaging system for measuring the diameter of the ball or core. It utilizes a plurality of high resolution digital cameras which capture images of the ball or core along multiple perpendicular planes and measure the diameter at sub-regional edges, the measurement of the sub-regions being controlled by a novel algorithm.

Another embodiment of the invention comprises a physical method of measuring the diameter, with a plurality of precisely opposed pairs of linear variable displacement transducers (LVDT). The probes are located over the poles of the ball or core and offset from the equator. Part of the inventive concept is comprised in the method of centering the ball between the probes. The probe tip face design has a concave radius which matches or is slightly greater than the diameter of the ball or core.

The apparatus of the present invention provides for an automated compression measurement of the dynamic compression measurement (DCM), soft core deflection index (SCDI) or effective modulus. The apparatus uses a precision controlled placement and a computer controlled servomotor in a compression measuring station. The ball or core is placed between an anvil and a load cell and sensors notify the apparatus when the ball or core is in position. Using a screw actuator driven by a servo motor, a compression force and deflection is imparted to the ball or core. Deflection is captured by an LVDT type measuring probe, such as a Novotechnik TRS25 position transducer, or the like. Load is captured by a load cell, such as an Omegadyne LC111-1K, or the like.

Also in accordance with the principles of the present invention, the apparatus includes a weight measurement station that records the weight by either a balance or load cell scale.

BRIEF DESCRIPTION OF THE DRAWINGS

The detailed description will be better understood in conjunction with the accompanying drawings, wherein like reference characters represent like elements, as follows.

DETAILED DESCRIPTION OF THE INVENTION

Figure 1:
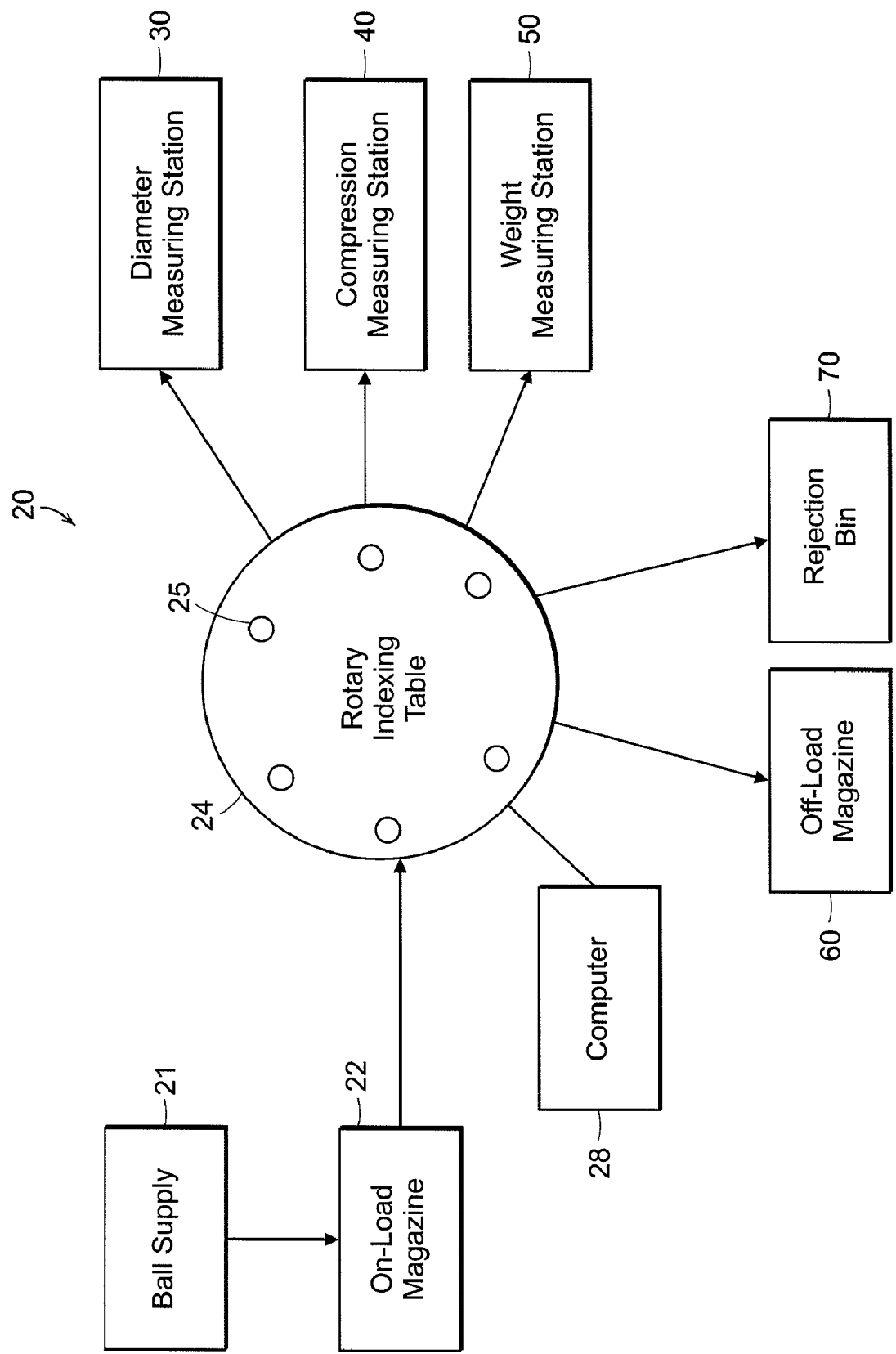
FIG. 1 is a schematic diagram of an automated measurement apparatus including automated testing stations arranged and formed in accordance with the principles of the present invention.

As shown schematically in FIG. 1, the present invention relates to an apparatus and method thereof of automating the testing of golf balls and cores wherein a plurality of tests for physical properties of the ball or core can be performed by one apparatus. Automated testing apparatus 20 permits continuous, objective testing of spheres, whether it is for golf balls or golf ball cores. The apparatus 20 is designed to accommodate both golf balls and cores ranging in size from 1.00 to 1.72 inches. Apparatus 20 not only provides important information for use in quality control, but also permits further automated actions to be taken with respect to the balls being processed, as described herein.

In a preferred manufacturing process according to the present invention, the testing apparatus 20 measures golf ball diameter, weight and compression and performs these tests at separate individual stations of the apparatus 20. Each individual measuring station has the ability to be selectively run or be bypassed. The apparatus will track each ball or core independently and report each ball's specific properties. A computer 28 compiles summary reporting which will include each ball's individual properties, averages of these properties, maximums, minimums, standard deviations and total out-of-round for any particular group.

The present invention automatically loads and unloads balls into and out of each station of the testing apparatus, therein saving time and keeping the balls in the order by which they were loaded. As stated above, the testing apparatus 20 is not limited to a particular diameter size, but will incorporate removable holding nests 26 which can be sized to accommodate a range of diameters, preferably from 1.0 inch to 1.72 inches.

Figure 2:
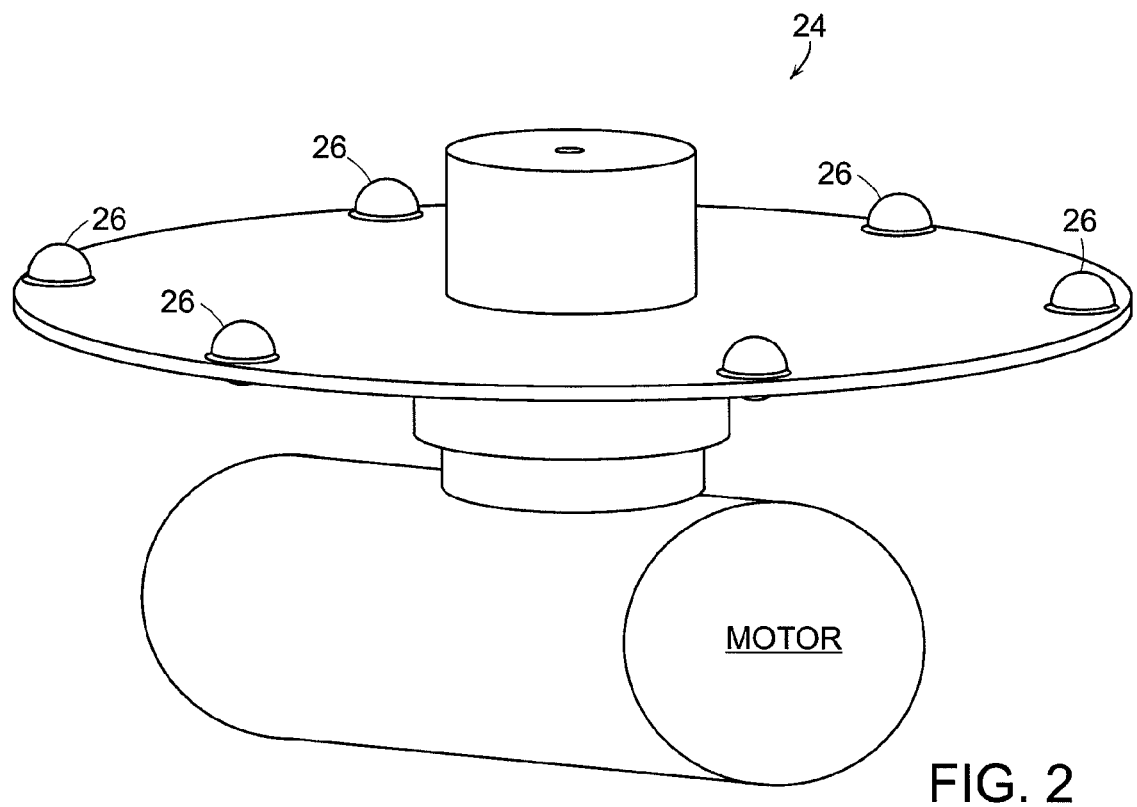
FIG. 2 is a perspective view of a rotary indexing table in accordance with the principles of the present invention.
Figure 3:
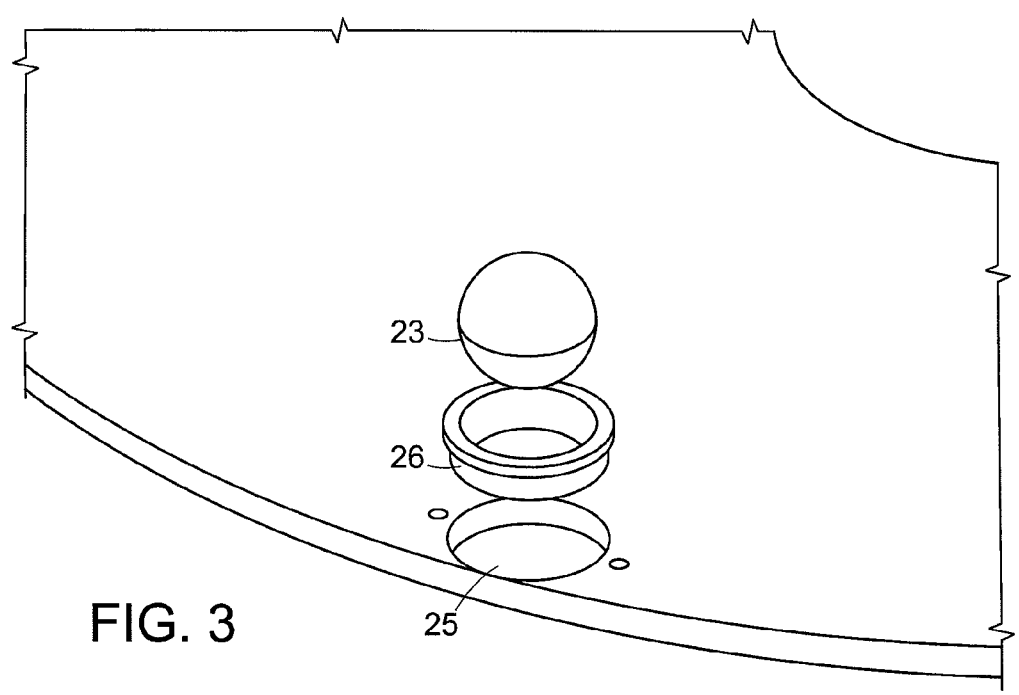
FIG. 3 is a detail of the relationship of the holding nest and a golf ball core to be tested with the rotary indexing table in accordance with the principles of the present invention.
Figure 4:
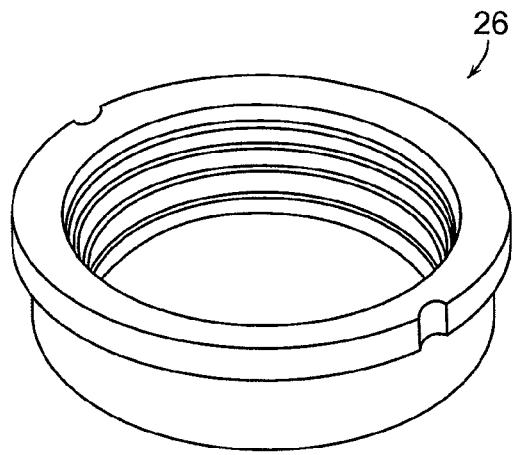
FIG. 4 is a pictorial view of a holding nest.

As shown in FIGS. 1-3, the apparatus 20 comprises a series of stations for the testing of the balls or cores 23. These stations are a diameter measuring station 30, a compression measuring station 40 and a weight measuring station 50. The first phase of the process is to deliver balls or cores form a supply source 21 to an on-load magazine 22, which is a device having a specified holding capacity for a multitude of golf balls. The computer 28 monitors the presence of balls or cores in the on-load magazine 22 utilizing presence sensors. The controller 28 then executes a command for an insertion of the sample into the apparatus utilizing pick and place suction cup servo style hardware and mechanisms (not shown) to accurately place the ball or core onto the rotary indexing table 24. The balls or cores 23 are cycled into and out of the apparatus in the order they were loaded, and they are accurately positioned into one of a plurality of removable holding nests 26 which have multiple ball sizing accommodations and are sized to friction fit within openings 25 in the indexing table 24. Prior to a ball or core actually being placed into one of the holding nests 26, and prior to any measurements being made, a blast of clean and dried compressed air (not shown) blows off any contaminants from the ball or core. A deionizer is employed to mitigate any static charge that may attract contamination.

As previously stated, the rotary indexing table 24 consists of a plurality of removable holding nests 26 (FIGS. 2 and 3) which have multiple ball sizing accommodations, and are installed into the rotary indexing table 24 for the purpose of securely capturing and presenting balls or cores to the various measuring stations. The holding nests 26 comprise: radius, multiple angles, multiple fingers or compliant inserts, in order to provide a robust method of holding balls in place while in motion between measurements. The removable holding nests 26 are of a slip-fit design and easily may be exchanged out of the openings 25 defined in the indexing table 24 to accommodate various ball and core diameters. The rotary indexing table 24 is capable of being dialed in order to place balls or cores accurately into each measurement position, such rotary motion provided by a motor such as an Alfa Series Indexing Unit 9AD-08277R-SR3VW1 (not shown). The computer 28 and various sensors (not shown) monitor when a ball or core is precisely loaded and when testing is completed at each measurement station.

Current methods of obtaining golf ball diameters are typically taken by hand at one specific location at a time. This is a time consuming method with poor repeatability, also the current methods of vision inspection do not offer the precision that is currently available with new high resolution digital cameras. The apparatus 20 of the present invention utilizes the diameter measurement station 30 which sizes the ball or core diameter by either vision or physical methods.

Figure 5:
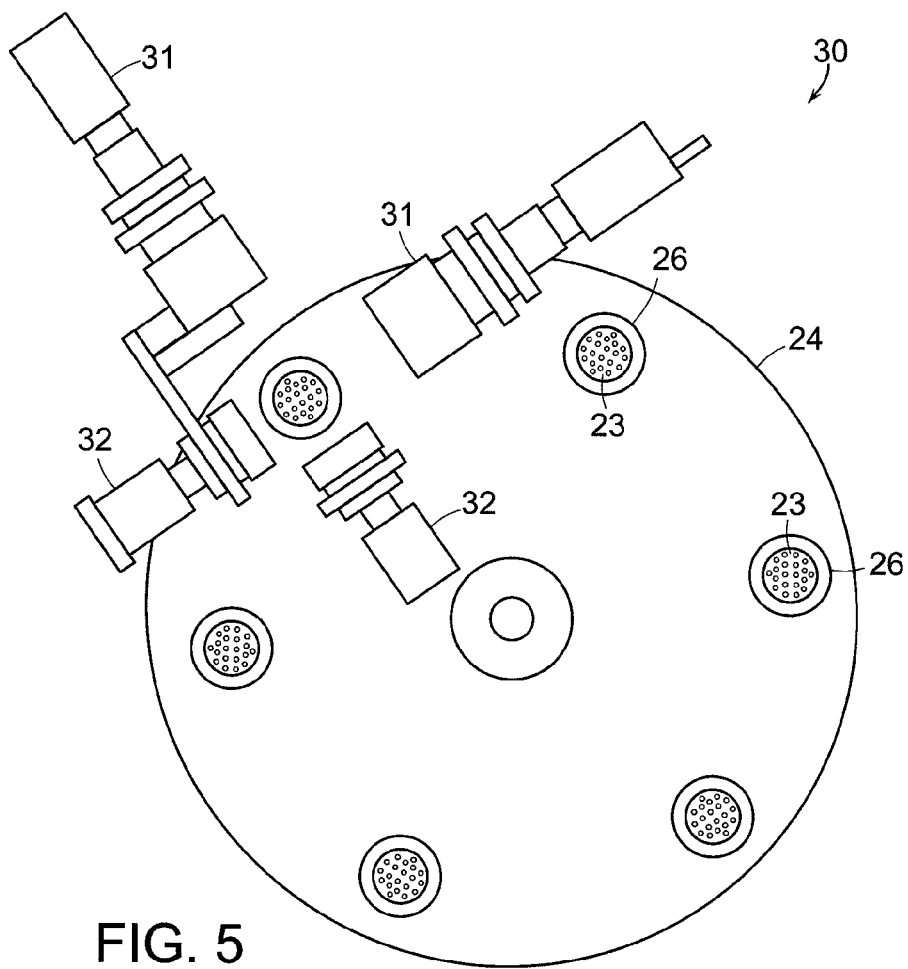
FIG. 5 is a top view of the diameter measuring station utilizing an Optical imaging method for measuring.
Figure 11:
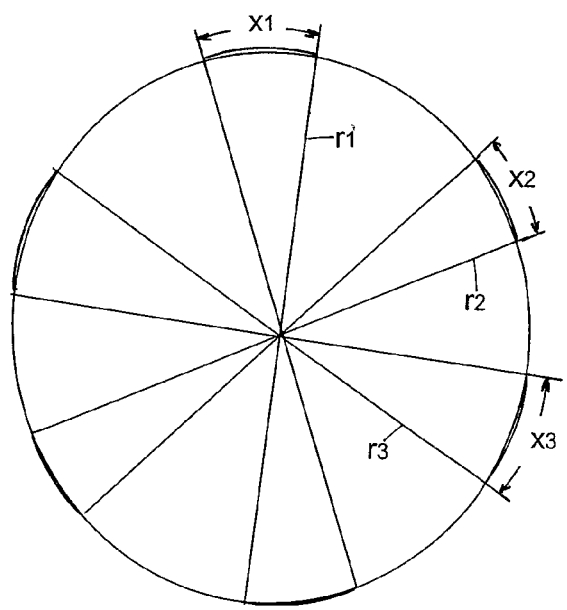
FIG. 11 is a view of a golf ball or core having multiple sub-regions.

An embodiment of the invention for the diameter measuring station 30 employs an optical or vision method for measuring ball or core diameters and ascertains these diameters at multiple ball locations using a multiple camera system (FIGS. 5 and 11). FIG. 5 depicts the use of a two high pixel count camera system, collimated back lighting and telecentric lens.

An algorithm is used to detect the edge of the ball. About 4800 edge points are divided into numerous segments of about 5 to 35 degrees, preferably twelve 30° segments. A typical segmented ball is shown in FIG. 11, wherein three segments x1, x2, and x3 are shown, resulting in radii r1, r2, and r3. The radius of each segment is added to its 180° counterpart to compute diameter. The two camera system is recommended to capture mold shift, equator, and pole dimensions. This enhances cycle time and measurement accuracy. The vision method provides for the rotary indexing table 24 to rotate and present the ball or core 23, which, as previously stated, is positioned in one of the holding nests 26, to be viewed by multiple cameras 32 that make the measurements for calculating the ball or core diameter. By utilizing a lifting mechanism, the ball or core is presented to the viewing area of the cameras 32 by elevating it through the holding nests 26 located in the rotary indexing table 24. Sensors notify the processor that the ball or core is in position to be measured. Using the two, high resolution digital cameras with pixel count of 2000×2000 or greater; lenses, preferably telecentric lenses; and a back-lighting source; digital images are captured along two perpendicular planes. Images are processed by computer using customized software to capture the edge of the ball and factor out the holding fingers. Custom algorithms detect the edges of the ball or core.

The captured image of a ball is best produced by backlighting with a red light-emitting diode (LED) in one line of sight direction. The edge of the resulting ball image can be analyzed using Mil development software such as that from Matrox Electronics Systems, Ltd. and broken into 5 to 35 degree sectors to measure out of roundness and average diameter of the golf ball in each plane. This remedies the problem of dimple edge irregularity by averaging over a 5 to 35 degree section of the ball. A steel ball is used for calibration wherein the image scene equates the number of pixels in the image to the number of inches on the calibrated steel ball. Telecentric lenses 31 keep the image size essentially constant for small positional changes along the line of sight. A 0.5 inch change in distance of object from lens amounts to 1.6 pixel change in diameter. The diameter of the ball is typically 1500 pixels for the 4 mega-pixel camera used.

As previously discussed, to create the exact silhouette of the ball in the image with sharp edges, it is desirable to use a collimated backlight 32 as a light source. Another means of collimating a more diffuse light source used in the present invention is to place the LED source some distance away from the ball, preferably about 39 inches. This procedure still allows the camera to use a F32 aperture setting for best depth and the exposure time of the camera for maximum contrast, which results in two 90 degree views simultaneously measuring the ball under inspection, utilizing a 1 inch square complimentary metal-oxide semiconductor (CMOS) image sensor with 4 million pixels, and collimating the light by either placing the light source 39 inches away or lens the light source to produce parallel rays of light.

Figure 6:
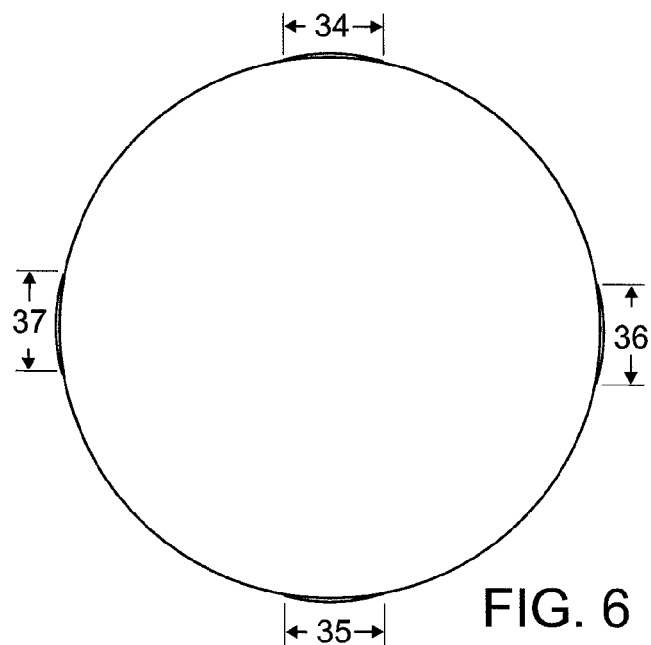
FIG. 6 is a view of a golf ball or core having four sub-regions calculated from an algorithm

Previous methods of determining ball size by non-contact image analysis entailed determining the edges of a ball image that was typically 2000×2000 pixels in size. The captured image was then processed by using the Shen-Castan algorithm found in MATROX imaging software package. Typically, the determination of edges of the total image took about 0.79 seconds. An embodiment of the present invention describes a vision image analysis utilizing a hi-speed image algorithm for measuring ball size, therein decreasing the time to size a golf ball or core by image analysis. FIG. 6 shows the segmenting of that multiple sub-regions, such as top 34, bottom 35, right 36, and left 37 on the golf ball and locating the perimeter edges in those sub-regions. Each sub-region contains only 200×200 pixels and transforms the edges found in these sub-sections to give the same ball statistics results as analyzing the much larger original captured image. This embodiment was found to take only 0.09 seconds for each ball captured. This improvement inn processing time results in processing nine times as many balls as with the prior computer procedure.

The inventive algorithm can be broken down into the following eight steps:

1.) In-putting the approximate global estimate of ball center and overall size;

2.) Copying into the image buffer the imaged sub-region of left edge of the ball from the knowledge of information in inputted in step 1, and finding the edges in first local coordinate system;

3.) Copying into the image buffer the imaged sub-region of right edge of ball from the knowledge of step 1, and finding the edges in second local coordinate system;

4.) Copying into the image buffer the imaged sub-region of top edge of ball from the knowledge of step 1, and finding the edges in third local coordinate system;

5.) Copying into the image buffer the imaged sub-region of bottom edge of ball from the knowledge of step 1, and finding the edges in fourth local coordinate system;

6.) Coordinating the four local coordinating measurements back to the global coordinating system;

7.) Finding the center of the ball by fitting global edge coordinates to circle; and, 8.) Measuring the average size of the ball at four regions from coordinates of edge points and center point found in step 7.

Figure 7:
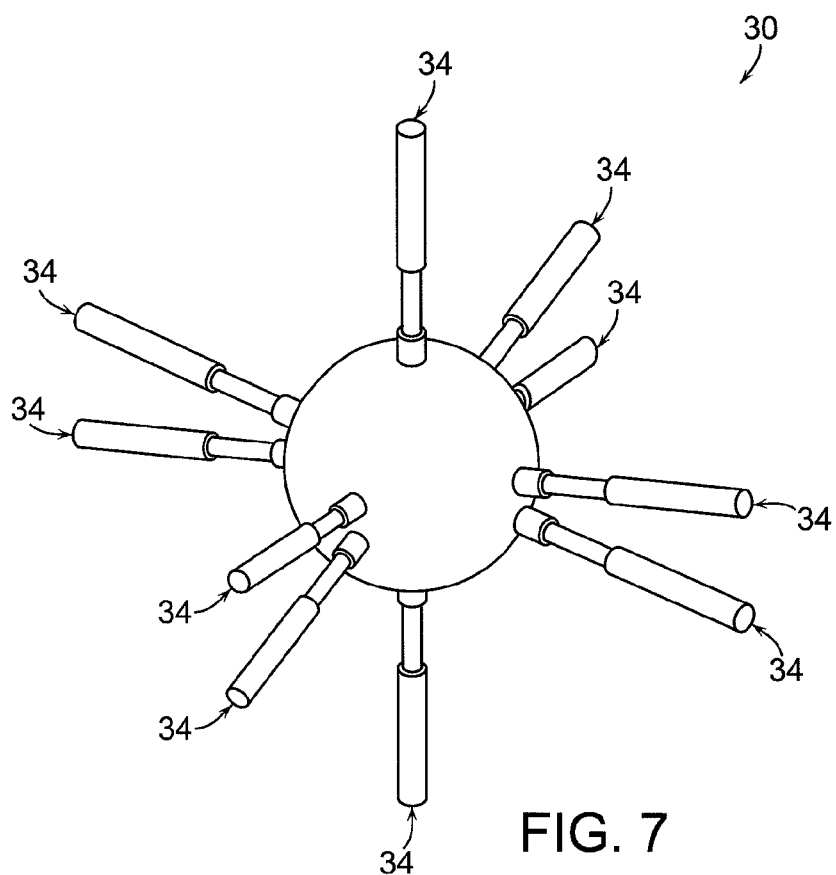
FIG. 7 is a pictorial view of the Physical imaging method for a measuring the diameter of a ball or core.
Figure 8:
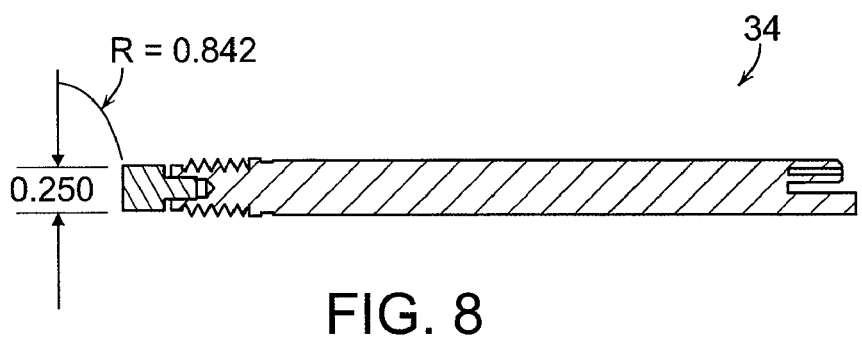
FIG. 8 is a cross sectional view of a probe of FIG. 6.

Another embodiment of the diameter measurement station 30 incorporates a physical sizing method which utilizes multiple probes 34. As with the vision system, the ball or core is presented to the probes 34 by elevating it through the holding nests 26 located in the rotary indexing table 24. Sensors notify the processor when the ball or core is in position to be measured. Diameter measurements are obtained using precisely opposed pairs of linear variable displacement transducer (LVDT) type measuring probes, (FIGS. 7 and 8) located over the poles of the ball or core 23 and offset from the equator. Compressed air is used to blow off station contaminants prior to any measurement. A cover (not shown) over this station 30 mitigates contamination which may affect measurement. A method of centering the ball between the probes is employed, such as an adjustable or replaceable nest. Probe tip face design has a concave radius 36 such to match or to be slightly greater than the diameter of the ball or core, i.e. if a golf ball measures 1.680", the concave face tip design may measure 1.680" to 1.683". Probe tip diameter shall be larger than the largest dimple size in order to catch the frets and not fall into the dimple. The probe system of the present invention utilizes a probe diameter of about 0.25 inch and is capable of measuring a ball diameter to within ±0.0005" using a probe such as a Solaris probe AX/2.5/922558 or the like. Information captured by the probes is processed into diameter measurement and stored by computer.

It is to be appreciated that the embodiment employing a vision method may be preferred over the embodiment employing a multiple probe system as the vision system is more impervious to debris or contamination due to its non-contacting operation.

Figure 9:
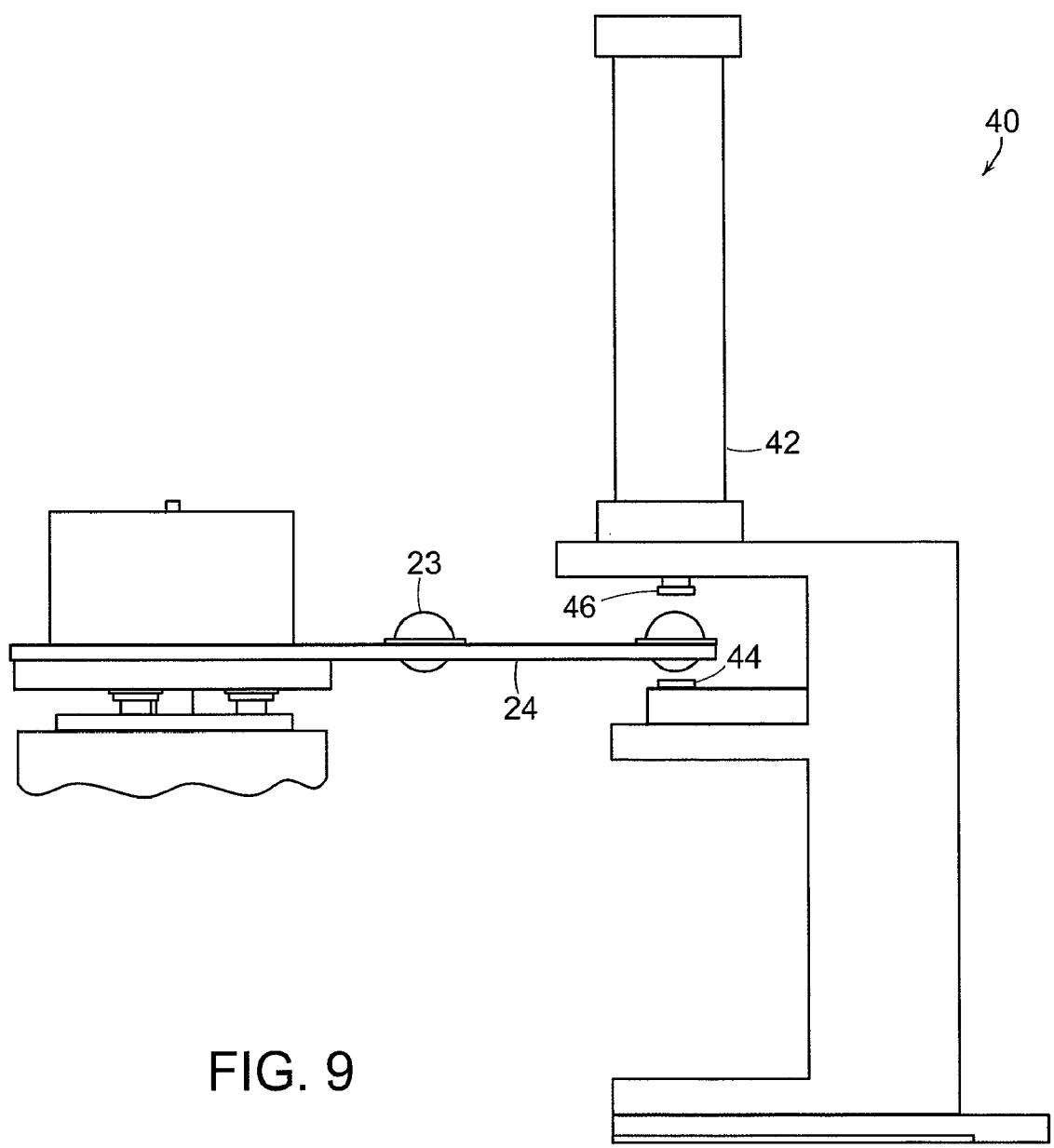
FIG. 9 is an elevational view of a compression station relative to the rotary indexing table.
Figure 10:
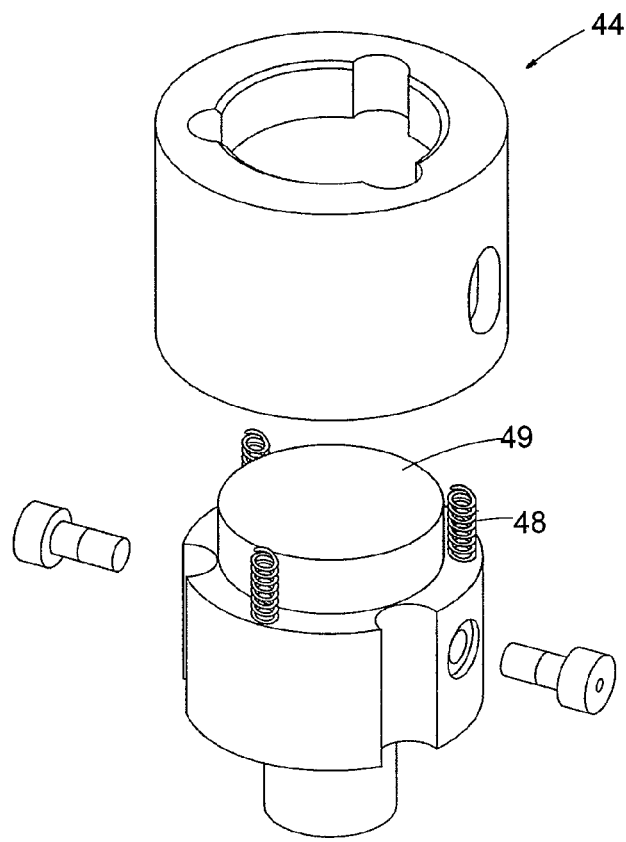
FIG. 10 is an expanded pictorial view of a positioning device having a spring loaded centering element.

The apparatus 20 also employs a compression station 40 (FIGS. 9 and 10) to automate the measurement of the ball or core soft core deflection index (SCDI) compression or effective modulus. Prior methods typically involved hand placement into a force-deflection measurement machine such as an Instron®. Other prior devices may employ a compressed air driven, hydraulic press with a load cell. These methods have a slow cycle and non-repeatable sample location, which may alter test results. As it is well known, hydraulic presses have unreliable test speeds due to the nature of hydraulics changing viscosity with temperature and wearing or leaking seals. The compression station 40, as viewed in FIG. 9, uses precision placement to locate the sample and has faster cycle rate. Testing speed is precisely controlled using a computer controlled servomotor (not shown). Speeds can be varied to provide a means for alternative testing.

The compression station 40 accepts a ball or core 23 from the rotary indexing table 24 by either lowering the table or by elevating the ball from below. The all or core 23 is placed in the compression station 40 between an upper positioned load cell 42 (LC114-1K) which has an anvil 46 mounted to it. A centering device 44 is employed on the bottom section in order to contain the sample's location. This feature is shown in greater detail on FIG. 10 and depicts an outer diameter that is loaded by springs 48 employed to center the ball or core, then, under light load, retract to allow a flat platen 49 to impart to the ball a concave shape. Sensors notify the processor that the ball or core 23 is in position to be measured. Utilizing a screw actuator driven ball by a servo motor (not shown), a load and deflection in imparted to a ball or core. Once the anvil 46 begins to contact the ball, a load deflection curve is recorded. Deflection is captured by a positive transducer such as a linear variable displacement transducer (LVDT) type measuring probe. Custom software records and calculates the load deflection curve. Should a new formula be developed in the future for specifying compression, a series of force-deflection data points are recorded for each ball, with a preferably number being about twelve points per deflection. This information is maintained in a database along with the test summaries.

The rate of compression can be controlled by software and a motor controller. The rate can be varied, depending on the test, from 1 to 60 inches per second. The distance a ball or core shall be compressed (displaced) will range typically form 0.001 to 0.500 inch. The load cell 42 has a capacity between 0 and 1000 pounds, and the linearity, repeatability and hysteresis are equal or less than 0.03% of full scale. Data reported from this station will be user selectable to include options of reporting force vs. deflection. Deflection at 100 kg, 130(−)10 kg, effective modulus, SCDI and Atti are the most commonly used. These options will be selected by the user. Specifically selected methods of reporting compression are available to report for each test.

The remaining measurement site of the apparatus 20 is a weight measurement station 50 which captures the weight of both balls and cores. The weighing station is not described or shown in detail as it employs a commercially available balance or load cell scale. The weight measuring station 50 can report mass of the ball or core in both grams and ounces. Units reported are two decimal places for grams (0.00 g) and three places for ounces (0.000 oz.). A balance scale similar in specification to those of a Mettler Toledo PG5002-S may be used.

Upon completion of the tests at the specified measurement stations 30, 40, and 50, a mechanism picks and sends the ball to either an offload station 60, if the ball or core has passed inspection, or to a reject bin 70 if it does not.

The invention described and claimed herein is not to be limited in scope by the specific embodiments herein disclosed, since these embodiments are intended solely as illustrations of several aspects of the invention. Any equivalent embodiments and various modifications apparent to those skilled in the art are intended to be within the scope of this invention. Such modifications are also intended to fall within the scope of the appended claims.

What is claimed is:

1. An apparatus for the automated testing of physical properties of golf balls or cores, the apparatus comprising:
   an on-load magazine for holding a multitude of balls or cores;
   a rotary indexing table having a plurality of removable holding nests, each nest having multiple ball sizing accommodations;
   means for transferring a ball or core from the on-load magazine to one of the plurality of removable holding nests;
   a computer controlled diameter measuring station comprising an optical measuring system using multiple high pixel count cameras, collimated back lighting, telecentric lenses that capture edge images of the golf ball or core in two perpendicular planes that segments about 4800 edge points on a golf ball perimeter wherein four sub-regions are segmented on the ball or core and he ball or core is measured by an algorithm comprising the following steps:
   a) establishing an approximate global estimate of the center location and size of the ball or core;
   b) copying into an image buffer an imaged sub-region of a left edge from a first local coordinate system of the ball or core from information in step (a);
   c) copying into an image buffer an imaged sub-region of a right edge from a second local coordinate system of the ball or core from information in step (a);
   d) copying into an image buffer an imaged sub-region of a top edge from a third local coordinate system of the ball or core from knowledge of information in step (a);
   e) copying into an image buffer an imaged sub-region of a bottom edge from a fourth local coordinate system of the ball or core from information in step (a);
   f) transforming the local coordinate measurements back to the global coordinate system;
   g) fitting global edge coordinates to a circle to find the center point of the ball or core; and
   h) measuring average size of the ball or core at four regions from coordinates of edge points and the center point contained in step (g);
   a compression measuring station;
   a weight measuring station; and
   a rotation device to position a ball or core into one of the measuring stations; and
   an offload magazine for collecting balls or cores that pass the testing and a rejection chute for balls or cores that do not.

2. The apparatus of claim 1, wherein the apparatus may selectively bypass one or more of the measuring stations.

3. The apparatus of claim 1, wherein the perimeter measuring system segments at least six sub-regions on the ball or core, each sub-region comprising a segment between 5 to 35 degrees.

4. The apparatus of claim 1, wherein the diameter measuring station comprises a physical contact method including a plurality of precisely opposed pairs of linear variable displacement transducer measuring probes located over the poles of the ball or core and offset from the equator.

5. The apparatus of claim 4, wherein the probe has a tip face design having a concave radius to be at least the diameter of the largest dimple size of the golf ball.

6. The apparatus of claim 1, wherein the compression measuring station comprises a positioning device having an anvil with a flat platen surface, and a spring loaded outer diameter used to first center the ball for the placement of the platen.

7. The apparatus of claim 6, wherein the pressing of the anvil upon the ball or core produces a deflection that is captured by a position transducer.

8. The apparatus of claim 1, wherein the weight measurement station captures the weight of the ball or core in either grams or ounces.

9. The apparatus of claim 1, wherein the removable multiple sized holding nests accommodate golf balls or cores ranging in size from 1.0 inches to 1.72 inches.

10. The apparatus of claim 1, wherein the transferring means comprises a servo with suction cup which picks a ball or core from the on-load magazine and places it into one of the nests.

11. A method of automatically testing a golf ball or golf ball core, which comprises the steps of:
    loading a multitude of golf balls or cores into an on-load magazine;
    picking a ball or core from the on-load magazine and subjecting it to a de-ionized air jet to remove debris and static charges;
    placing the ball or core into a removable holding nest defined in a rotary indexing table;
    rotating the table to a computer controlled diameter measuring station comprising an optical measuring system that segments a plurality of sub-regions on the golf ball or core and measures the diameter of ball or core by an algorithm comprising the steps:
    a) establishing an approximate global estimate of the center location and size of the ball or core;
    b) copying into an image buffer an imaged sub-region of a left edge from a first local coordinate system of the ball or core from information in step (a);
    c) copying into an image buffer an imaged sub-region of a right edge from a second local coordinate system of the ball or core from information in step (a);
    d) copying into an image buffer an imaged sub-region of a top edge from a third local coordinate system of the ball or core from knowledge of information in step (a);
    e) copying into an image buffer an imaged sub-region of a bottom edge from a fourth local coordinate system of the ball or core from information in step (a);
    f) transforming the local coordinate measurements back to the global coordinate system;
    g) fitting global edge coordinates to a circle to find the center point of the ball or core; and
    h) measuring average size of the ball or core at a plurality of perimeter sub-regions from coordinates of edge points and the center point contained in step (g);
    rotating the table to a compression measuring station to measure the hardness and deflection of the ball or core;
    rotating the table to a weight measuring table to measure the mass of the ball or core; and
    picking and placing the ball or core to either an offload magazine if the ball or core passes testing or to a rejection bin if it does not pass.

12. The method of claim 11, wherein at least one of the measuring stations may be selectively omitted.

13. The method of claim 11, wherein the diameter measuring station comprises an optical measuring system using two high resolution digital cameras having telecentric lenses that capture edge images along two perpendicular planes of the ball or core, wherein the captured images are produced by a collimated backlighting in one line of sight direction.

14. The method of claim 11, wherein the diameter measuring station comprises a physical contact method wherein a plurality of precisely opposed pairs of linear variable displacement transducer measuring probes are located over the poles of the ball or core and offset from the equator.

15. The method of claim 14, wherein the probe has a tip diameter larger than the largest dimple size of the golf ball.

16. The method of claim 11, wherein the compression measuring station comprises positioning a ball between and anvil and a load cell.

17. The method of claim 16, wherein the pressing of the anvil upon the ball or core produces a deflection that is captured by a linear variable displacement transducer type probe.

18. The method of claim 11, wherein the multiple sized holding nests can accommodate golf balls or cores ranging in size from 1.0 inches to 1.72 inches.

19. A method of using an algorithm to detect four edge segments of a golf ball or core, the algorithm comprising the steps of:
    a) establishing an approximate global estimate of the center location and size of the ball or core;
    b) copying into an image buffer an imaged sub-region of a left edge from a first local coordinate system of the ball or core from information in step (a);
    c) copying into an image buffer an imaged sub-region of a right edge from a second local coordinate system of the ball or core from information in step (a);
    d) copying into an image buffer an imaged sub-region of a top edge from a third local coordinate system of the ball or core from knowledge of information in step (a);
    e) copying into an image buffer an imaged sub-region of a bottom edge from a fourth local coordinate system of the ball or core from information in step (a);
    f) transforming the local coordinate measurements back to the global coordinate system;
    g) fitting global edge coordinates to a circle to find the center point of the ball or core; and
    h) using a computer for measuring average size of the ball or core at four regions from coordinates of edge points and the center point contained in step (g).

* * * * *